(12) United States Patent
Ramesh et al.

(10) Patent No.: US 6,699,943 B2
(45) Date of Patent: Mar. 2, 2004

(54) WATER-BASED COATING COMPOSITION HAVING CARBAMATE-MELAMINE CROSS-LINKING, METHOD OF PREPARING THE SAME, AND A CURED FILM THEREOF

(75) Inventors: Swaminathan Ramesh, Canton, MI (US); Paul Lessek, Elk Point, SD (US); Wolfgang Bremser, Münster (DE)

(73) Assignee: BASF Corporation, Southfield, MI (US)

( * ) Notice: Subject to any disclaimer, the term of this patent is extended or adjusted under 35 U.S.C. 154(b) by 432 days.

(21) Appl. No.: 09/747,473

(22) Filed: Dec. 22, 2000

(65) Prior Publication Data

US 2003/0220439 A2 Nov. 27, 2003

(51) Int. Cl.[7] .................. C08L 53/02; C08F 226/02
(52) U.S. Cl. .................. 525/329.9; 525/330.5; 525/191; 525/193; 525/194; 525/95; 525/98; 524/598; 526/301
(58) Field of Search .................. 525/329.9, 330.5, 525/191, 193, 194, 95, 98; 524/598; 526/301

(56) References Cited

U.S. PATENT DOCUMENTS

| | | | |
|---|---|---|---|
| 5,356,669 A | 10/1994 | Rehfuss et al. | 427/407.1 |
| 5,552,497 A | 9/1996 | Taylor et al. | 525/456 |
| 5,567,527 A | 10/1996 | Webster et al. | 428/412 |
| 5,684,078 A | 11/1997 | Pfaffenschlager et al. | 524/457 |
| 5,756,213 A | 5/1998 | Ohrbom et al. | 428/412 |
| 5,786,420 A | 7/1998 | Grandhee | 525/7 |
| 5,827,931 A | 10/1998 | Menovcik et al. | 525/453 |
| 5,854,385 A | 12/1998 | McGee et al. | 528/369 |
| 5,856,382 A | 1/1999 | Ohrbom et al. | 523/414 |
| 5,989,642 A * | 11/1999 | Singer et al. | 427/407.1 |
| 6,040,062 A | 3/2000 | McGee et al. | 428/500 |
| 6,045,872 A | 4/2000 | Harmon et al. | 427/407.1 |
| 6,060,556 A | 5/2000 | Collins et al. | 524/533 |
| 6,150,465 A | 11/2000 | Harris et al. | 525/163 |
| 6,346,591 B1 | 2/2002 | Ohrbom et al. | 526/312 |
| 2002/0035289 A1 | 3/2002 | Ohrbom et al. | 560/157 |
| 2002/0086966 A1 | 7/2002 | Weise et al. | 526/312 |
| 2002/0103319 A1 | 8/2002 | Ohrbom et al. | 526/312 |

FOREIGN PATENT DOCUMENTS

| | | | |
|---|---|---|---|
| EP | 755 946 | 7/1996 | C08F/2/22 |
| EP | 0 761 695 | 8/1996 | C08F/8/00 |
| EP | 899 103 | 8/1998 | B41J/2/045 |
| WO | WO 99/62978 | 12/1999 | C08F/293/00 |

OTHER PUBLICATIONS

English Language Internatinal Search Report PCT/US01/42953, International Filing Date Nov. 19, 2001.
English Language International Search Report PCT/US01/44459, International Filing Date Nov. 27, 2001.

* cited by examiner

Primary Examiner—James J. Seidleck
Assistant Examiner—Olga Asinovsky

(57) ABSTRACT

The present invention is directed to a curable, water-based coating composition utilized in waterborne coating systems. The coating composition is the reaction product of a water-based copolymer prepared by free-radical polymerization, and a cross-linking agent. The copolymer is the reaction product of a first block and a second block. The first block is the reaction product of a first ethylenically unsaturated monomer, acrylic acid, and a second ethylenically unsaturated monomer, methyl methacrylate, as well as the reaction product of a vinylaromatic hydrocarbon monomer, diphenylethylene. The second block is the reaction product of a plurality of ethylenically unsaturated monomers, styrene, 2-ethylhexyl methacrylate, cyclohexyl methacrylate, and carbonate-modified glycidyl methacrylate including a carbonate functional group that is subsequently converted into a carbamate functional group by ammonium hydroxide. The cross-linking agent, preferably a melamine, reacts with the carbamate functional group to establish a coating composition having urethane cross-linking from the carbamate—melamine reaction.

58 Claims, No Drawings

WATER-BASED COATING COMPOSITION HAVING CARBAMATE-MELAMINE CROSS-LINKING, METHOD OF PREPARING THE SAME, AND A CURED FILM THEREOF

RELATED APPLICATIONS

This patent application claims priority to and all advantages of German Application No. 10029803.6, entitled "Clearcoat Material And Its Use To Produce Clearcoats And Multicoat Color And/Or Effect Coating Systems," which was filed on Jun. 16, 2000.

FIELD OF THE INVENTION

The subject invention generally relates to a curable, water-based coating composition utilized primarily in waterborne coating systems, such as waterborne basecoat (WBBC) systems, waterborne clearcoat (WBCC) systems, and waterborne primer systems. More specifically, the coating composition includes a water-based copolymer, having a carbamate functional group, and a cross-linking agent that is reactive with the carbamate functional group and dispersible in water. The subject invention also relates to a method of preparing the coating composition as well as a method of preparing a cured film of the coating composition.

BACKGROUND OF THE INVENTION

Water-based coating compositions include water-based copolymers and cross-linking agents as components. The water-based copolymers are desirable for use in coating systems in the automotive and industrial coatings industries because these copolymers enable formulation of waterborne coating systems, such as WBBC, WBCC, and waterborne primer systems. It is known in the art that waterborne coating systems are ideal as compared to solventborne coating systems because waterborne coating systems have lower content of volatile organic compounds (VOCs).

The water-based copolymers of the prior art have proven to be inadequate for use as a component in water-based coating compositions. The water-based copolymers of the prior art are ineffective because these copolymers are highly viscous, as secondary dispersions, and generally have poorly defined film forming characteristics, as primary dispersions. Furthermore, the cross-linking between these copolymers and select conventional cross-linking agents are often particularly susceptible to environmental acid etch.

The water-based copolymers of the prior art are also deficient because these copolymers often incorporate additional components such as co-solvents and increased amounts of surfactants which are both undesirable components in waterborne coating systems. For instance, conventional water-based copolymers typically incorporate a co-solvent to promote dispersibility of the copolymer in water, and these co-solvents contribute to increased VOCs. Conventional water-based copolymers also typically incorporate increased amounts of surfactants directly into the copolymer to achieve and maintain miscibility and incorporation of the copolymer in water, and as understood by those skilled in the art, use of increased amounts of surfactants in the coating composition frequently contributes to water sensitivity, humidity, and 'cratering' as well as other coating defects detrimental to the appearance of the waterborne coating system.

The free-radical polymerization methods of preparing the water-based copolymers of the prior art are also deficient. These conventional methods are typically highly exothermic and are therefore difficult to predict and control. The unpredictability of these methods leads to uncontrollable and inconsistent physical properties of the water-based copolymer and ultimately of the water-based coating composition which includes the copolymer as a component. More specifically, the unpredictability of these methods frequently leads to inconsistent molecular weight distribution of the copolymer, and to incomplete conversion of monomer components into the copolymer. Furthermore, in the preparation of conventional water-based copolymers, distribution of the monomer components is random and does not produce a 'tailored' polymeric architecture that is able to meet particular needs depending on whether the copolymer is utilized in a WBBC, WBCC, or waterborne primer system. It is understood in the art that inconsistent molecular weights, incomplete conversion of monomer components, and even random distribution of the monomer components affects, among other things, the stability of the viscosity of the copolymer and can even result in 'gelling' of the copolymer and of the water-based coating composition. Additionally, poor appearance characteristics of the WBBC, WBCC, or waterborne primer system, such as gloss and distinctness of image (DOI), can result from poor rheology, i.e., flow, of the coating composition upon application that is due to the inconsistencies in the water-based copolymer.

In sum, the prior art water-based copolymers which are components of the water-based coating composition, as detailed above, are characterized by one or more inadequacies. Due to the inadequacies identified in the prior art, it is desirable to provide a novel water-based copolymer and coating composition to be utilized in WBBC, WBCC, and waterborne primer systems as well as a novel method of preparing the coating composition and a cured film.

SUMMARY OF THE INVENTION

A curable, water-based coating composition is disclosed. The water-based coating composition of the subject invention is the reaction product of a water-based copolymer (A) and at least one water-dispersible cross-linking agent (B). The water-based copolymer (A) is prepared by free-radical polymerization and includes a first block polymer, or first block, (A)(I) and a second block (A)(II). The first block (A)(I) is preferably a hydrophilic block, and the second block (A)(II) is preferably a hydrophobic block. More specifically, the first block (A)(I) of the copolymer (A) is the reaction product of at least one ethylenically unsaturated monomer (A)(I)(a), and at least one vinylaromatic hydrocarbon monomer (A)(I)(b). The second block (A)(II) of the copolymer (A) is the reaction product of a plurality of ethylenically unsaturated monomers (A)(II)(a) different than the ethylenically unsaturated monomer (A)(I)(a), wherein at least one of the plurality includes at least one carbonate functional group for modification into a carbamate functional group. The cross-linking agent (B) is reactive with the carbamate functional group and is dispersible in water.

In the preferred water-based coating composition of the subject invention, the at least one ethylenically unsaturated monomer (A)(I)(a) of the first block (A)(I) is further defined as a first and second ethylenically unsaturated monomer where the first ethylenically unsaturated monomer is preferably acrylic acid, and the second ethylenically unsaturated monomer is preferably methyl methacrylate. Furthermore, the at least one vinylaromatic hydrocarbon monomer (A)(I)(b) of the first block (A)(I) is preferably diphenylethylene. Also in the preferred embodiment, the plurality of ethylenically unsaturated monomers (A)(II)(a) of the second block (A)(II) that are different than the at least one ethylenically unsaturated monomer (A)(I)(a) are styrene, 2-ethylhexyl methacrylate, cyclohexyl methacrylate, and carbonate-modified glycidyl methacrylate having the carbonate functional group. In the preferred embodiment, the carbonate functional group of the carbonate-modified glycidyl methacrylate is modified by an ammonia-containing compound, preferably ammonium hydroxide, into the carbamate functional group. Finally, the preferred water-dispersible cross-linking agent (B) that is reactive with the carbamate functional group is hexamethoxymethyl melamine.

A method of preparing the water-based coating composition is also disclosed. According to this method, the first block (A)(I) is first formed. Next, the second block (A)(II), having the at least one carbonate functional group, is polymerized with the first block (A)(I) to establish the water-based copolymer (A). The at least one carbonate functional group is then converted into at least one carbamate functional group. The copolymer (A) is then combined with the water-dispersible cross-linking agent (B) such that the cross-linking agent (B) reacts with the carbamate functional group to form the water-based coating composition of the subject invention.

The general object of the subject invention is to develop a water-based coating composition for use in WBBC, WBCC, and waterborne primer systems that utilizes carbamate—melamine cross-linking through a water-based copolymer (A), having a carbamate functional group, and a cross-linking agent (B) reactive with the carbamate functional group. It is also a general object to introduce a water-based coating composition that is completely solvent-free, i.e., does not utilize any co-solvents, such that the content of VOCs is zero while maintaining the dispersibility of the copolymer (A) in water without any co-solvents.

It is a further object of the subject invention to develop a water-based coating composition that includes a lower cost cross-linking agent (B) reactive with the carbamate functional group such that the WBBC, WBCC, and waterborne primer systems prepared from the water-based coating composition of the subject invention are resistant to environmental acid etch. It is a further object of the subject invention to develop a water-based coating composition primarily including a copolymer (A) that is surfactant-free, yet still fully miscible in water, such that the WBBC, WBCC, and waterborne primer systems that utilize the copolymer (A) in the water-based coating composition are crater resistant and do not suffer from other surfactant-related defects.

Regarding the method of preparing the water-based coating composition, it is an object of the subject invention to introduce a novel method that thoroughly converts monomer components into the copolymer (A) and that is predictable and controllable such that the structure of the copolymer (A) can be 'tailored' and achieved. Therefore, water-based coating compositions prepared according to the method of the subject invention maintain stable viscosities and result in cured films in either a WBBC, a WBCC, or a waterborne primer system having ideal appearance characteristics.

DETAILED DESCRIPTION OF THE INVENTION

The curable, water-based coating composition of the subject invention is utilized in waterborne coating systems. Waterborne coating systems, such as waterborne basecoat (WBBC) systems and waterborne clearcoat (WBCC) systems, are used throughout automotive, industrial, and other coatings industries to coat various substrates for aesthetic and functional purposes, such as color and environmental resistance, respectively. Although the subject invention is directed at WBBC and WBCC systems, it is to be understood that the subject invention may also be utilized in other waterborne coating systems including, but not limited to waterborne primer systems, and in other industries including, but not limited to, the adhesive and sealant industries.

The water-based coating composition of the subject, invention includes the reaction product of a water-based copolymer (A), having at least one carbamate functional group, and of at least one cross-linking agent (B) reactive with the carbamate functional group to establish urethane (—NH—CO—O—) cross-linking without use of an isocyanate. The water-based coating composition is prepared by a free-radical polymerization method. In general, the method of preparing the coating composition includes the steps of forming a first block (A)(I), polymerizing a second block (A)(II) with the first block (A)(I) to establish the water-based copolymer (A), converting a carbonate functional group of the copolymer (A) into a carbamate functional group, and combining the water-based copolymer (A) with the cross-linking agent (B) to form the water-based coating composition of the subject invention. These method steps will be discussed in greater detail below.

The water-based copolymer (A) is the reaction product of the first block (A)(I) and the second block (A)(II). In the most preferred embodiment, the first block (A)(I) is a hydrophilic block, and the second block (A)(II) is a hydrophobic block, and the subject invention will be described with this in mind. However, it is to be understood that the number of blocks, as described two blocks, is not intended to be limiting. For instance, the water-based copolymer (A) could also be the reaction product of three blocks, e.g. a first hydrophilic block, a second hydrophilic block, and a first hydrophobic block.

The first block (A)(I) is present in an amount from 5 to 15, preferably from 7 to 10, parts by weight based on 100 parts by weight of the coating composition. The first block (A)(I) is the reaction product of at least one ethylenically unsaturated monomer (A)(I)(a) and of at least one vinylaromatic hydrocarbon monomer (A)(I)(b). More specifically, to form the first block (A)(I), the at least one ethylenically unsaturated monomer (A)(I)(a) and at least one vinylaromatic hydrocarbon monomer (A)(I)(b) are polymerized. This polymerization step is conducted over time from 1 to 8, preferably from 2 to 7, and most preferably from 4 to 6, hours, and at a temperature between 50° C. and 100° C. It is to be understood that the time required to conduct this 'polymerization step' includes the time needed for the addition of monomer components as well as any holding or cooling time, where the addition of monomers may not be occurring. It is also to be understood that certain ethylenically unsaturated monomers (A)(I)(a) and certain vinylaromatic hydrocarbon monomers (A)(I)(b) require that the polymerization step be conducted under pressure. If required, such pressure is preferably from 1.5 to 3000 bar, and more preferably from 10 to 1000 bar.

The at least one ethylenically unsaturated monomer (A)(I)(a) of the first block (A)(I) is selected primarily to ensure the solubility of the copolymer (A) in water. As such, the at least one ethylenically unsaturated monomer (A)(I)(a) is selected to form a salt when reacted with a neutralizing agent. The neutralizing agent will be discussed further below. In addition to the primary purpose of ensuring the solubility of the copolymer (A) in water, the at least one ethylenically unsaturated monomer (A)(I)(a) may also be selected to achieve an ideal minimum film forming temperature, MFFT, for the water-based copolymer (A), and ultimately for a cured film of the water-based coating composition utilized in either the WBBC, WBCC, or waterborne primer system, such that the cured film is resistant to excessive cracking, chipping, and the like. The at least one ethylenically unsaturated monomer (A)(I)(a) may also be selected to minimize the photo-sensitivity of the coating composition and of the cured film formed of the coating composition.

In the preferred embodiment of the subject invention, the at least one ethylenically unsaturated monomer (A)(I)(a) is further defined as a first and second ethylenically unsaturated monomer. The first and second ethylenically unsaturated monomers are selected in order to balance the desired physical characteristics as discussed above. That is, the first and second ethylenically unsaturated monomers are selected to balance the solubility of the copolymer (A) in water as well as the MFFT and the photosensitivity of the coating composition and of the cured film. In terms of the total monomer composition in the first block (A)(I) of the copolymer (A), the first and second ethylenically unsaturated monomers form from 70 to 99, preferably from 90 to 96, parts by weight based on 100 parts by weight of total monomer composition in the first block A)(I). It is to be understood that, in addition to the content of the first and second ethylenically unsaturated monomers, the total monomer composition in the first block (A)(I) also includes the content of the at least one vinylaromatic hydrocarbon monomer (A)(I)(b). As will be discussed in greater detail below, in certain embodiments, the at least one vinylaromatic hydrocarbon monomer (A)(I)(b) is alternatively defined as at least one ethylenically unsaturated monomer (A)(I)(b) that is different than the at least one ethylenically unsaturated monomer (A)(I)(a) and of the general formula $R_1R_2C=CR_3R_4$. In such embodiments, the total monomer composition in the first block (A)(I) is defined to include the content of the at least one ethylenically unsaturated monomer (A)(I)(b) of the general formula $R_1R_2C=CR_3R_4$. In the preferred embodiment, the weight ratio of the first ethylenically unsaturated monomer to the second ethylenically unsaturated monomer in the first block (A)(I) is from 1:0.5 to 1:5.

The first ethylenically unsaturated monomer is selected from the group of compounds consisting of alkyl acrylic acids. The second ethylenically unsaturated monomer is selected from the group of compounds consisting of aliphatic acrylates, aliphatic methacrylates, cycloaliphatic acrylates, cycloaliphatic methacrylates, and mixtures thereof of each of these compounds. It is to be understood that each of these compounds include an alkyl radical, and in the preferred embodiment of the subject invention, each of these compounds includes up to 20 carbon atoms in the alkyl radical.

The alkyl acrylic acids that may be selected as the first ethylenically unsaturated monomer are selected from the group consisting of acrylic acid, methacrylic acid, ethacrylic acid, maleic acid, fumaric acid, itaconic acid, crotonic acid, and mixtures thereof. The aliphatic acrylates that may be selected as the second ethylenically unsaturated monomer are selected from the group consisting of methyl acrylate, ethyl acrylate, propyl acrylate, butyl acrylate, hexyl acrylate, ethylhexyl acrylate, stearyl acrylate, lauryl acrylate, and mixtures thereof The aliphatic methacrylates that may be selected as the second ethylenically unsaturated monomer are selected from the group consisting of methyl methacrylate, ethyl methacrylate, propyl methacrylate, butyl methacrylate, hexyl methacrylate, ethylhexyl methacrylate, stearyl methacrylate, lauryl methacrylate, and mixtures thereof. The cycloaliphatic acrylate that may be selected as the second ethylenically unsaturated monomer is cyclohexyl acrylate, and the. cycloaliphatic methacrylate that may be selected as the second ethylenically unsaturated monomer is cyclohexyl methacrylate.

In the most preferred embodiment of the subject invention, the first ethylenically unsaturated monomer is acrylic acid, and the second ethylenically unsaturated monomer is methyl methacrylate. Furthermore, the weight ratio of the acrylic acid to the methyl methacrylate in the first block (A)(I) is from 1:0.5 to 1:3 in the most preferred embodiment.

The at least one vinylaromatic hydrocarbon monomer (A)(I)(b) of the first block (A)(I) is selected from the group consisting of α-methylstyrene, diphenylethylene, dinapthaleneethylene, and mixtures thereof. Further, it is to be understood that other α-alkylstyrenes may be selected as the at least one vinylaromatic hydrocarbon monomer (A)(I)(b) as well as other equivalent compounds including, but not limited to, cis- or trans-stilbene, vinylidenebis (4-N,N-dimethylaminobenzene), vinylidenebis (4-aminobenzene), or vinylidenebis (4-nitrobenzene). Although more than one vinylaromatic hydrocarbon monomer (A)(I)(b) may be included in the first block (A)(I), the preferred embodiment of the subject invention includes only one vinylaromatic hydrocarbon monomer, most preferably diphenylethylene. In terms of the total monomer composition in the first block (A)(I) of the copolymer (A), the vinylaromatic hydrocarbon monomer forms from 1 to 20, preferably from 3 to 7, parts by weight based on 100 parts by weight of total monomer composition in the first block (A)(I).

In certain embodiments, the at least one vinylaromatic hydrocarbon monomer (A)(I)(b) of the first block (A)(I) may alternatively be defined as the at least one ethylenically unsaturated monomer (A)(I)(b) that is different than the at least one ethylenically unsaturated monomer (A)(I)(a) and that is of the general formula

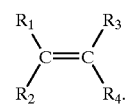

In these embodiments, the radicals $R_1$, $R_2$, $R_3$, and $R_4$, each independently of one another are hydrogen atoms or substituted or unsubstituted alkyl, cycloalkyl, alkylcycloalkyl, cycloalkylalkyl, aryl, alkylaryl, cycloalkylaryl, arylalkyl or arylcycloalkyl radicals, with the proviso that at least two of the variables $R_1$, $R_2$, $R_3$, and $R_4$ are substituted or unsubstituted aryl, arylalkyl or arylcycloalkyl radicals, especially substituted or unsubstituted aryl radicals.

Examples of suitable alkyl radicals are methyl, ethyl, propyl, isopropyl, n-butyl, isobutyl, tert-butyl, amyl, hexyl, or 2-ethylhexyl.

Examples of suitable cycloalkyl radicals are cyclobutyl, cyclopentyl, or cyclohexyl.

Examples of suitable alkylcycloalkyl radicals are methylenecyclohexane, ethylenecyclohexane, or propane 1,3-diylcyclohexane.

Examples of suitable cycloalkylalkyl radicals are 2-, 3-, or 4-methyl-, -ethyl-, -propyl-, or -butylcyclohex-1-yl.

Examples of suitable aryl radicals are phenyl, naphthyl or biphenylyl, preferably phenyl and naphthyl, and especially phenyl.

Examples of suitable alkylary radicals are benzyl or ethylene- or propane-1,3-diylbenzene.

Examples of suitable cycloalkylaryl radicals are 2-, 3-, or 4-phenylcyclohex-1-yl.

Examples of suitable arylalkyl radicals are 2-, 3-, or 4-methyl-, -ethyl, -propyl-, or -butylphen-1-yl.

Examples of suitable arylcycloalkyl radicals are 2-, 3-, or 4-cyclohexylphen-1-yl.

The above-described radicals $R_1$, $R_2$, $R_3$, and $R_4$ may be substituted. The substituents used may comprise electron-withdrawing or electron-donating atoms or organic radicals. Examples of suitable substituents are halogen atoms, especially chlorine and fluorine, nitrile groups, nitro groups, partially or fully halogenated, especially chlorinated and/or fluorinated alkyl, cycloalkyl, alkylcycloalkyl, cycloalkylalkyl, aryl, alkylaryl, cycloalkylaryl, arylalkyl and arylcycloalkyl radicals, including those exemplified above, especially tert-butyl; aryloxy, alkyloxy and cycloalkyloxy radicals, especially phenoxy, naphthoxy, methoxy, ethoxy, propoxy, butyloxy or cyclohexyloxy; arylthio, alkylthio and cycloalkylthio radicals, especially phenylthio, naphthylthio, methylthio, ethylthio, propylthio, butylthio or cyclohexylthio; hydroxyl groups; and/or primary, secondary and/or tertiary amino groups, especially amino, N-methylamino, N-ethylamino, N-propylamino, N-phenylamino, N-cyclohexylamino N,N-dimethylamino, N,N-diethylamino, N,N-dipropylamino, N,N-diphenylamino, N,N,-dicyclohexylamino, N-cyclo-hexyl-N-methylamino and N-ethyl-N-methylamino.

Examples of ethylenically unsaturated monomers (A)(I)(b) whose use is particularly preferred in these embodiments are diphenylethylene, dinaphthaleneethylene, cis- or trans-stilbene, vinylidenebis (4-N,N-dimethylamino-benzene), vinylidenebis (4-aminobenzene), and vinylidenebis (4-nitrobenzene).

Also, in accordance with these embodiments, ethylenically unsaturated monomers (A)(I)(b) may be used individually or as a mixture of at least two monomers (A)(I)(b).

Finally, as with the preferred embodiment which includes the at least one vinylaromatic hydrocarbon monomer (A)(I)(b), the preferred ethylenically unsaturated is monomers (A)(I)(b) in these alternative embodiments is diphenylethylene.

The subject invention will be described below only in terms of the at least one vinylaromatic hydrocarbon monomer (A)(I)(b).

In addition to the at least one ethylenically unsaturated monomer (A)(I)(a) and the at least one vinylaromatic hydrocarbon monomer (A)(I)(b), the first block (A)(I) is also the reaction product of the neutralizing agent. That is, the neutralizing agent is added to the at least one ethylenically unsaturated monomer (A)(I)(a) and to the at least one vinylaromatic hydrocarbon monomer (A)(I)(b) to form the first block (A)(I) of the water-based copolymer (A). Specifically, the neutralizing agent is selected from the group consisting of dimethylethanolamine, amino methyl propanol, ammonia, and mixtures thereof. It is to be understood that other base neutralizing agents may selected including, but not limited to, sodium hydroxide, potassium hydroxide, diethanolamine, triethanolamine, and mono-, di-, or tri-ethylamine. In the preferred embodiment, the neutralizing agent is ammonia, $NH_3$. The ammonia, $NH_3$, interacts with an acid group of the first ethylenically unsaturated monomer. More specifically, in the preferred embodiment, the ammonia, $NH_3$, interacts with the hydrogen atom of the —COOH group of the acrylic acid, to form a salt of the acrylic acid, having a —COO group, i.e., an acid anion group, and $NH_4^+$. The salt of acrylic acid ensures the solubility of the copolymer (A) in water.

Like the neutralizing agent, an initiator, also known a polymerization promoter, is added to the at least one ethylenically unsaturated monomer (A)(I)(a) and to the at least one vinylaromatic hydrocarbon monomer (A)(I)(b) to form the first block (A)(I) of the water-based copolymer (A). The initiator initiates the free-radical polymerization process. The initiator is soluble in water and is selected from the group consisting of inorganic persulfates, dialkyl peroxides, hydroperoxides, peresters, and mixtures thereof. In the preferred embodiment of the subject invention, the initiator is an inorganic persulfate selected from the group consisting of ammonium persulfate, $(NH_4)_2S_2O_8$, potassium persulfate, $K_2S_2O_8$, and sodium persulfate, $Na_2S_2O_8$. Most preferably, the initiator is ammonium persulfate. However, in alternative embodiments, the free-radical polymerization initiator may be a dialkyl peroxides such as di-tert-butyl peroxide or dicumyl peroxide, a hydroperoxide such as cumene hydroperoxide or tert-butyl hydroperoxide, or a perester, such as tert-butyl perbenzoate, tert-butyl perpivalate, tert-butyl per-3,4,5,-trimethylhexanoate or tert-butyl per-2-ethylhexanoate.

The weight ratio of the initiator to the at least one vinylaromatic hydrocarbon monomer (A)(I)(b) is preferably from 1:3 to 3:1. It is to be understood that it is preferred to add comparatively large amounts of the initiator. More specifically, it is preferred that the initiator be present in an amount from 0.5 to 50, more preferably from 1.0 to 20, and most preferably from 3 to 10, parts by weight based on 100 parts by weight of total monomer composition in the first block (A)(I). At the completion of the formation of the first block (A)(I), the first block (A)(I) has a non-volatile content of from 20 to 40, preferably from 25 to 35, percent non-volatile by weight. Furthermore, the completed first block (A)(I) has a number average molecular weight, $M_n$, from 1,000 to 20,000, preferably from 3,000 to 10,000.

Next, monomers making up the second block (A)(II), which have at least one carbonate functional group, are polymerized with the first block (A)(I) to establish the water-based copolymer (A). This polymerization step, between the monomers making up the second block (A)(II) and the first block (A)(I), is conducted over time from 1 to 8, preferably from 5 to 6, hours, and at a temperature between 50° C. and 100° C., more preferably between 80° C. and 100° C. As with the polymerization step for forming the first block (A)(I), it is to be understood that the time required to conduct this 'polymerization' step includes the time needed for the addition of monomer components as well as any holding or cooling time, where the addition of monomers may not be occurring. Also, for this polymerization step, preferably no additional free-radical initiator is required. Instead, this polymerization step is preferably initiated by self-formation of radicals. Also, in this polymerization step, the at least one vinylaromatic hydrocarbon monomer (A)(I)(b) of the first block (A)(I), in the preferred embodiment diphenylethylene, controls the polymerization of the incoming monomers that make up the second block (A)(II). The second block (A)(II) of the copolymer (A) is more specifically the reaction product of a plurality of ethylenically unsaturated monomers (A)(II)(a) that can be different than the ethylenically unsaturated monomer (A)(I)(a), and are present in an amount from 25 to 50, preferably from 32 to 43, parts by weight based on 100 parts by weight of the coating composition.

The plurality of ethylenically unsaturated monomers (A)(II)(a) are hydrophobic, i.e., insoluble in water, and in preparing the second block (A)(II) of the copolymer (A), the plurality of ethylenically unsaturated monomers (A)(II)(a) are selected to promote miscibility between the coating composition and other components commonly utilized in WBBC, WBCC, and waterborne primer systems. The plurality of ethylenically unsaturated monomers (A)(II)(a) are also selected to contribute to the MFFT for the water-based copolymer (A), and ultimately for the cured film of the water-based coating composition utilized in either the WBBC, WBCC, or waterborne primer systems.

At least one of the ethylenically unsaturated monomers of the plurality (A)(II)(a) includes at least one carbonate functional group. As such, the plurality of ethylenically unsaturated monomers (A)(II)(a) are selected from the group consisting of styrene, butyl acrylate, butyl methacrylate, 2-ethylhexyl methacrylate, 2-hydroxyethyl methacrylate, cyclohexyl methacrylate, glycidyl acrylate, glycidyl methacrylate, carbonate-modified glycidyl acrylate, carbonate-modified glycidyl methacrylate, and mixtures thereof, so long as the plurality of ethylenically unsaturated monomers (A)(II)(a) that are selected are different than the ethylenically unsaturated monomer (A)(I)(a).

Also, as discussed above, at least one of the plurality (A)(II)(a) must introduce the carbonate functional group. Therefore, one of either carbonate-modified glycidyl acrylate or carbonate-modified glycidyl methacrylate is to be selected. Of course, it is understood that alternative carbonate-modified compounds can be introduced by other chemical compounds such as epoxy group containing compounds reacted with $CO_2$, and even by chemical compounds having unsaturated bonds that are first converted to an epoxy group by known reactions with peroxides. Once these chemical compounds have been modified to include a carbonate functional group, the carbonate functional group can then be converted into a carbamate functional group as will be described in greater detail below.

As also understood by those skilled in the art, the carbonate-modified glycidyl acrylate is formed by the reaction of glycidyl acrylate, having the chemical formula of $CH_2{:}CHCOOCH_2\underline{CHCH_2O}$, with $CO_2$, under excessive pressure and temperature conditions. Similarly, the carbonate-modified glycidyl methacrylate is formed by the reaction of glycidyl methacrylate, having the chemical formula of $CH_2{:}C(CH_3)COOCH_2\underline{CHCH_2O}$, with $CO_2$, under excessive pressure and temperature conditions. In the most preferred embodiment, the plurality of ethylenically unsaturated monomers (A)(II)(a) that are selected are styrene, 2-ethylhexyl methacrylate, cyclohexyl methacrylate, and carbonate-modified glycidyl methacrylate which includes the carbonate functional group. For descriptive purposes, the common chemical name for carbonate-modified glycidyl methacrylate is 4-(hydroxymethyl)-1,3-dioxolan-2-one methacrylate and the accepted chemical abstract chemical name is 2-propenoic acid, 2-methyl-, (2-oxo-1,3-dioxalan-4-yl) methyl ester.

After the second block (A)(II) is polymerized with the first block (A)(I) to establish the water-based copolymer (A), the carbonate functional group in the second block (A)(II) of the copolymer (A) is then modified, i.e., converted, into the carbamate functional group. More specifically, at a temperature between 50° C. and 100° C., more preferably between 50° C. and 70° C., an ammonia-containing, $NH_3$, compound is reacted with the carbonate functional group to convert the carbonate functional group into the carbamate functional group. This reaction step, between the ammonia-containing compound and the carbonate functional group, is conducted over time from 1 to 4 hours.

The ammonia-containing compound is selected from the group consisting of ammonia, ammonium hydroxide, and mixtures thereof. As understood by those skilled in the art, use of either ammonia or ammonium hydroxide to convert the carbonate functional group results in a primary carbamate functional of the general formula $NH_2COO—$. Additionally, a primary amine can be used to convert the carbonate functional group. Use of the primary amine results in a secondary carbamate functional group of the general formula $NHRCOO—$, where R is an alkyl radical. However, in terms of the preferred embodiment of the subject invention, reaction with the primary amine is not preferred because secondary carbamate functional groups exhibit 'sluggish' reactions with the preferred cross-linking agent (B) which will be discussed below. Although in the preferred embodiment the carbonate functional group is converted into the carbamate functional group after the second block (A)(II) is polymerized with the first block (A)(I), it is to be understood that, alternatively, the carbonate functional group can be converted into the carbamate functional group prior to polymerization of the second block (A)(II) with the first block (A)(I).

In the preferred embodiment, ammonium hydroxide is utilized to convert the carbonate functional group into the carbamate functional group. The ammonia, $NH_3$, group of the ammonium hydroxide can form a primary carbamate functional group having a primary hydroxyl (—OH) group which is shown schematically below.

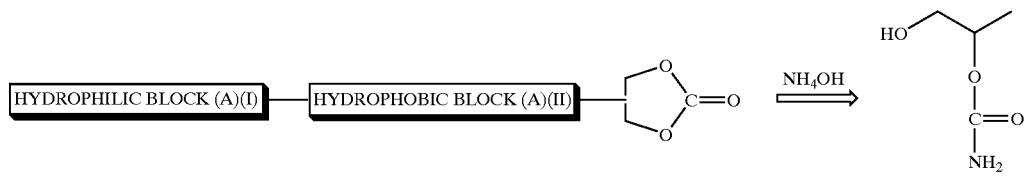

Alternatively, the ammonia, $NH_3$, group of the ammonium hydroxide can form a primary carbamate functional group having a secondary hydroxyl (—OH) group which is shown schematically below.

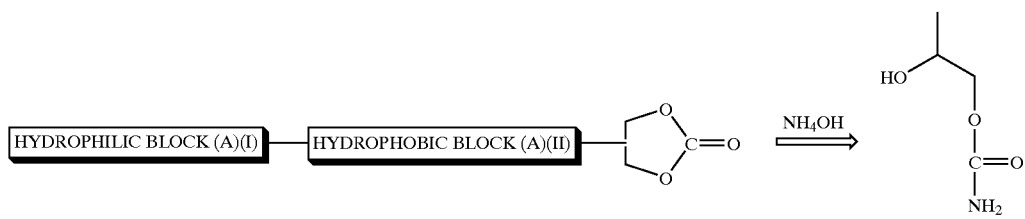

The water-based coating composition is also the reaction product of the at least one cross-linking agent (B) that is reactive with the carbamate functional group and that is dispersible in water. It is to be understood that dispersibility in water indicates that the cross-linking agent (B) can be mixed into water to produce a homogenous mixture of the cross-linking agent (B) and the water with no phase separation between the two components. The water-based copolymer (A) is combined with the cross-linking agent (B) to form the coating composition of the subject invention. More specifically, small amounts, from 0.1 to 3 parts by weight based on 100 parts by weight of the total coating composition, of an anionic surfactant are added with the copolymer (A) and the cross-linking agent (B) to guarantee the dispersibility of the cross-linking agent (B) in water. Preferably, a sulfonate-based surfactant is selected as the anionic surfactant.

The cross-linking agent (B) is selected from the group consisting of water-dispersible aminoplasts, water-dispersible polymers having acrylamide groups, and water-dispersible polymers having methylol or alkoxymethyl groups, and mixtures thereof. Furthermore, the cross-linking agent (B) is present in an amount from 0.1 to 10, preferably from 0.05 to 5, and most preferably from 1 to 3, parts by weight based on 100 parts by weight of the coating composition.

It is to be understood that the water-dispersible aminoplasts include urea resins and melamine formaldehyde resins. The melamine formaldehyde resins of the preferred embodiment include either a methylol group, $CH_2OH$, an alkoxymethyl group, or both. The alkoxymethyl group is of the general formula $-CH_2OR_1$, where $R_1$ is an alkyl chain having from 1 to 20 carbon atoms. As understood by those skilled in the art, the methylol groups and the alkoxymethyl groups are reactive with the carbamate functional group.

Possible cross-linking agents include, but are not limited to, monomeric and polymeric melamine formaldehyde resins, including both partially and fully alkylated melamines such as methylated melamines, butylated melamines, and methylated/butylated melamines. Other cross-linking agents (B) that are urea resins include methylol ureas such as urea formaldehyde resins, and alkoxy ureas such as butylated urea formaldehyde resin.

The preferred embodiment of the subject invention includes hexamethoxymethyl melamine (HMMM). HMMM is commercially available from Monsanto under its Resimene Amino Crosslinker Resins. HMMM is shown in the following chemical representation.

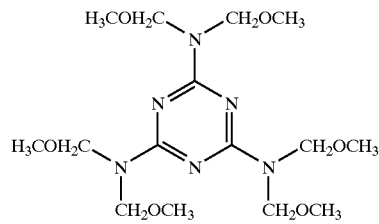

Upon addition of the cross-linking agent (B) to the copolymer (A), the alkoxymethyl groups of the H specifically the $CH_2OCH_3$ group, reacts with the carbamate functional group in the second block (A)(II) of the copolymer (A) to establish a urethane (—NH—CO—O—) linkage without use of an isocyanate. The urethane linkage between the copolymer (A) and the cross-linking agent (B) is from the carbamate-melamine reaction and is ideal for resistance to environmental acid etch. Overall, the copolymer (A) has a number-average molecular weight, $M_n$, of from 5,000 to 2,000,000. Additionally, the coating composition of the subject invention has a non-volatile content of from 20 to 60, preferably from 30 to 50, percent non-volatile by weight, and an average volume particle size of $\leq 200$ nm.

The cured film of the water-based coating composition of the subject invention is prepared by applying the water-based coating composition to the substrate. More specifically, the water-based coating composition can be sprayed onto the substrate by air-atomized or bell-applied spray application, and other equivalent processes. Once applied to the substrate, the coating composition is cured to form the cured film. Although cross-linking may occur prior to the curing step, the cross-linking agent (B) completely reacts with the at least one carbamate functional group during the curing step to form the cured film of the water-based coating composition including the urethane cross-linking. Preferably, the reaction between the cross-linking agent (B) and the carbamate functional group occurs at a temperature between 100° C. and 175° C., and more preferably at a temperature between 110° C. and 130° C. from 20 to 30 minutes.

It is to be understood that all of the preceding chemical representations are merely two-dimensional chemical representations and that the structure of these chemical representations may be other than as indicated.

The following examples, illustrating the formation of the first block (A)(I), the formation of an initial form of the copolymer (A), the formation of the complete copolymer (A), the formation of the coating composition, and of the cured film of the coating composition, as presented herein, are intended to illustrate and not limit the invention.

EXAMPLES

Example 1

The first block (A)(I) of the copolymer (A) was prepared by adding and reacting the following parts, by weight, unless otherwise indicated.

TABLE 1

| First Block (A)(I) Reactant | Amount (grams) |
|---|---|
| Acrylic acid | 203.6 |
| Methyl methacrylate | 366.9 |
| Diphenylethylene | 29.9 |
| Ammonia | 198.3 |
| Ammonium persulfate | 45.1 |
| DI water | 1156.3 |
| % Non-Volatile | 32.9% |

Per the above table, Table 1, 1051.3 grams of de-ionized water were added to a reaction flask. The reaction flask, preferably a steel reactor, was equipped with a stirrer and a reflux condenser. The reaction flask, including the water, was heated via a conventional heat supply to a temperature of 90° C. Next, three feed streams from three independent feed vessels were fed into the water in the reaction flask over approximately 4 to 5 hours to form the first block (A)(I) of the copolymer (A). More specifically, the first feed stream included 203.6 grams of acrylic acid, 366.9 grams of methyl methacrylate, and 29.9 grams of diphenylethylene. The second feed stream included 198.3 grams of the neutralizing agent ammonia, and the third feed stream included 105.0 grams of water and 45.1 grams of the initiator ammonium persulfate. During the addition of the three feed streams into the reaction flask containing water, satisfactory reflux was achieved. Further, after the addition of the three feed streams, the temperature of the reaction flask increased from 90° C. to 94° C.–96° C. thus indicating an exotherm, and then the temperature of the reaction flask returned to 90° C. The batch was maintained at 90° C. for an additional two hours. After this, the heat supply was removed from the reaction flask and the first block (A)(I), formed by the polymerization of the acrylic acid, the methyl methacrylate, and the diphenylethylene, as well as by the ammonia and the ammonium persulfate, was allowed to cool. The percent non-volatile of the first block (A)(I) was determined to be 32.9%.

Example 2

Next, an initial form of the copolymer (A) was formed by polymerizing the second block (A)(II) with the first block (A)(I) prepared in Example 1 above. This polymerization step included the following parts, by weight, unless otherwise indicated.

TABLE 2

| Initial Water-Based Copolymer (A) | Detail | Amount (grams) |
|---|---|---|
| FIRST BLOCK (A)(I) | [FROM EXAMPLE 1 ABOVE] | 181.5 |
| SECOND BLOCK A(II) | Styrene | 157.9 |
|  | 2-ethylhexyl methacrylate | 177.6 |
|  | cyclohexyl methacrylate | 198.8 |
|  | carbonate-modified glycidyl methacrylate | 126.6 |
| WATER | — | 1032.4 |

Per the above table, Table 2, 1032.4 grams of water were added to a reaction flask. The reaction flask, including the water, was heated via a conventional heat supply to a temperature of 90° C. for approximately 30 minutes. Next, 181.5 grams of the first block (A)(I), from Example 1, was added to the reaction flask including the water. Following the complete addition of first block (A)(I), a feed stream of the second block (A)(II) was added to the reaction flask. More specifically, the second block (A)(II) feed stream included 157.9 grams of styrene, 177.6 grams of 2-ethylhexyl methacrylate, 198.8 grams of cyclohexyl methacrylate, and 126.6 grams of carbonate-modified glycidyl methacrylate. This feed stream was added to the reaction flask, including the water and the first block (A)(I), over approximately 5 to 6 hours, and the temperature of the reaction flask fluctuated between 90° C. and 94° C. throughout the addition of the second block (A)(II) feed stream. The polymerization of the second block (A)(II) with the first block (A)(I) completed the formation of the initial form of copolymer (A) of the subject invention.

Example 3

In Example 3, the carbonate functional group of the initial form of copolymer (A) was converted into the carbamate functional group according to the following parts, by weight, unless otherwise indicated.

TABLE 3

| Water-Based Copolymer (A) | Detail | Amount (grams) |
|---|---|---|
| INITIAL WATER-BASED COPOLYMER (A) | [FROM EXAMPLE 2 ABOVE] | 200.0 |
| AMMONIUM HYDROXIDE | NH$_4$OH | 20.2 |
| WATER | — | 1.0 |
| % Non-Volatile | — | 41.3% |
| Initial Physical Property Integrity of Copolymer (A) | Standard 2 mil Thickness Drawdown Air Dry | (1) Film wet, soft, and somewhat gelled (2) No resistance to 'double rubs' with methyl ethyl ketone (MEK) |

Per the above table, Table 3, 200.0 grams of the initial form of copolymer (A), from Example 2 above, and 1.0 gram of de-ionized water were added into a reaction flask. The reaction flask, including the water, was heated via a conventional heating supply to a temperature of 60° C. Next, 15.2 grams of ammonium hydroxide were added into the reaction flask over approximately 1 to 2 hours. During this addition, the temperature in the reaction flask fluctuated between 60° C. and 80° C. After the addition of the 15.2 grams of ammonium hydroxide, the extent of the carbonate-to-carbamate conversion was verified by a known method, specifically infrared (IR) spectroscopy. It was determined that some carbonate functionality remained. As such, an additional 5.0 grams of ammonium hydroxide were added into the reaction flask at 60° C. over approximately 0.5 hours to complete the conversion of the carbonate functional group to the carbamate functional group.

The completed copolymer (A) of Example 3, including both the first block (A)(I) and the second block (A)(II), and including the carbamate functional group converted from the carbonate functional group had a percent non-volatile of 41.3%. Furthermore, the initial physical property integrity of the copolymer (A) was evaluated by verifying resistance to a strong solvent, i.e., resistance to MEK double rubs, of a 2 mil thickness drawdown under air dry conditions. The result of the initial physical property integrity is included in Table 2. As understood by those skilled in the art, the MEK double rub method is an acceptable method for initial verification of the integrity of an air-dried or oven-cured film.

Example 4

In Example 4, the completed copolymer (A) and the cross-linking agent (B) were added to form the coating composition of the subject invention. The coating composition as depicted in this example is merely a preliminary 'scale-up' intended to equal coating compositions utilized in WBBC, WBCC, and waterborne primer systems that may include other components such as pigments, flow additives, catalysts, UV-resistance packages, and the like. The coating composition was prepared according to the following parts, by weight, unless otherwise indicated.

TABLE 4

| Coating Composition | Sample A Amount (grams) |
|---|---|
| COMPLETED COPOLYMER (A) (FROM EXAMPLE 3) [W/ CARBONATE CONVERTED TO CARBAMATE] | 200.0 |
| hexamethoxymethyl melamine (HMMM) Cross-Linking Agent (B) | 3.0 |
| Anionic Surfactant | 1.0 |
| Total | 204.0 |
| Stability Instant | No viscosity Increase |
| Stability After 24 Hours | No viscosity Increase |
| Sprayability of Coating Composition | -Acceptable |
| Appearance of Cured Film | -Acceptable -Uniform -Slight Peel |
| Initial Physical Property Integrity of Cured Film (after spray applied to substrate, and then a cure at 250° F. (121.1° C.) for 30 minutes) | (1) Cured film dry, hard, and not gelled (2) Resistance of greater than 150 cycles of MEK 'double rubs' |

Per the above table, Table 4, the coating composition (Sample A) was formed by the addition, at room temperature, of 200 grams of the copolymer (A) and 3.0 grams of the cross-linking agent hexamethoxymethyl melamine (HMMM). More specifically, the copolymer (A) was first added into a container, and then the cross-linking agent (B) was added into the container, including the copolymer (A), under mixing. Additionally, a small amount of anionic surfactant, specifically 1.0 gram, was incorporated to guarantee the dispersibility of the HMMM in water.

After the addition, under mixing, of the cross-linking agent, Sample A was evaluated for stability. For instant stability, i.e., immediately after the addition of the cross-linking agent (B), Sample A did not show any significant increase in viscosity. For stability after a 24 hour time period, the result was the same, no significant viscosity increase.

Furthermore, Sample A was spray applied to a substrate, specifically ACT e-coated panels, and then cured to form the cured film of the subject invention. The 'sprayability' of Sample A was evaluated as acceptable primarily because the sample had a workable spray viscosity. As for the curing step, Sample A was cured in a conventional oven at 250° F. for 30 minutes, and then the cured film of coating composition was evaluated for appearance and initial physical property integrity.

The general appearance of the cured film was uniform and acceptable. Sample A had a slight 'peel.' Finally, the initial physical property integrity of the cured film of Sample A was evaluated after the cure of 250° F. for 30 minutes. The results of the initial physical property integrity of the cured film of Sample A was acceptable and is included above in Table 4.

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

What is claimed is:

1. A curable, water-based coating composition comprising the reaction product of:
   (A) a water-based copolymer prepared by free-radical polymerization, said copolymer comprising the reaction product of;
      (I) a first block comprising the reaction product of;
         (a) at least one ethylenically unsaturated monomer, and
         (b) at least one vinylaromatic hydrocarbon monomer; and
      (II) a second block comprising the reaction product of;
         (a) a plurality of ethylenically unsaturated monomers different than (A)(I)(a), wherein at least one of said plurality includes at least one carbonate functional group for modification into a carbamate functional group; and
   (B) at least one cross-linking agent reactive with said carbamate functional group and dispersible in water.

2. A coating composition as set forth in claim 1 wherein said at least one cross-linking agent (B) is selected from the group consisting of water-dispersible aminoplasts, water-dispersible polymers having acrylamide groups, and water-dispersible polymers having methylol or alkoxymethyl groups, and mixtures thereof.

3. A coating composition as set forth in claim 2 wherein said water-dispersible aminoplasts are selected from the group of melamine formaldehyde resins having a methylol group, an alkoxymethyl group, or both, which are reactive with said carbamate functional group.

4. A coating composition as set forth in claim 1 further including an ammonia-containing compound reactive with said ethylenically unsaturated monomer of said plurality (A)(II)(a) that includes said carbonate functional group, said ammonia containing compound modifying said carbonate functional group into said carbamate functional group.

5. A coating composition as set forth in claim 4 wherein said ethylenically unsaturated monomer of said plurality (A)(II)(a) that includes said carbonate functional group is selected from the group consisting of carbonate-modified glycidyl acrylate, carbonate-modified glycidyl methacrylate, and mixtures thereof.

6. A coating composition as set forth in claim 4 wherein said ammonia-containing compound is selected from the group consisting of ammonia, ammonium hydroxide, and mixtures thereof.

7. A coating composition as set forth in claim 1 wherein said first block (A)(I) is present in an amount from 5 to 15 parts by weight based on 100 parts by weight of said coating composition.

8. A coating composition as set forth in claim 1 wherein said second block (A)(II) is present in an amount from 25 to 50 parts by weight based on 100 parts by weight of said coating composition.

9. A coating composition as set forth in claim 1 wherein said at least one cross-linking agent is present in an amount from 0.1 to 10 parts by weight based on 100 parts by weight of said coating composition.

10. A coating composition as set forth in claim 1 wherein said first block (A)(I) further comprises the reaction product of a neutralizing agent.

11. A coating composition as set forth in claim 10 wherein said neutralizing agent is selected from the group consisting of dimethylethanolamine, amino methyl propanol, ammonia, and mixtures thereof.

12. A coating composition as set forth in claim 1 wherein said first block (A)(I) further comprises the reaction product of an initiator.

13. A coating composition as set forth in claim 12 wherein said initiator is selected from the group consisting of inorganic persulfates, dialkyl peroxides, hydroperoxides, peresters, and mixtures thereof.

14. A coating composition as set forth in claim 12 wherein the weight ratio of said initiator to said at least one vinylaromatic hydrocarbon monomer (A)(I)(b) is from 1:3 to 3:1.

15. A coating composition as set forth in claim 1 wherein said at least one ethylenically unsaturated monomer (A)(I)(a) is further defined as a first and second ethylenically unsaturated monomer.

16. A coating composition as set forth in claim 15 wherein said first ethylenically unsaturated monomer is acrylic acid.

17. A coating composition as set forth in claim 16 wherein said second ethylenically unsaturated monomer is methyl methacrylate.

18. A coating composition as set forth in claim 15 wherein said first ethylenically unsaturated monomer is selected from the group of compounds consisting of alkyl acrylic acids, and said second ethylenically unsaturated monomer is selected from the group of compounds consisting of aliphatic acrylates, aliphatic methacrylates, cycloaliphatic acrylates, cycloaliphatic methacrylates, and mixtures thereof, wherein each of said first and second ethylenically unsaturated monomers include up to 20 carbon atoms in the alkyl radical.

19. A coating composition as set forth in claim 18 wherein the weight ratio of said first ethylenically unsaturated monomer to said second ethylenically unsaturated monomer is from 1:0.5 to 1:5.

20. A coating composition as set forth in claim 1 wherein said at least one ethylenically unsaturated monomer (A)(I)(a) is selected from the group of compounds consisting of aliphatic acrylates, aliphatic methacrylates, cycloaliphatic acrylates, cycloaliphatic methacrylates, alkyl acrylic acids, and mixtures thereof, each of said compounds having up to 20 carbon atoms in the alkyl radical.

21. A coating composition as set forth in claim 20 wherein said aliphatic acrylates are selected from the group consisting of methyl acrylate, ethyl acrylate, propyl acrylate, butyl acrylate, hexyl acrylate, ethylhexyl acrylate, stearyl acrylate, lauryl acrylate, and mixtures thereof.

22. A coating composition as set forth in claim 20 wherein said aliphatic methacrylates are selected from the group consisting of methyl methacrylate, ethyl methacrylate, propyl methacrylate, butyl methacrylate, hexyl methacrylate, ethylhexyl methacrylate, stearyl methacrylate, lauryl methacrylate, and mixtures thereof.

23. A coating composition as set forth in claim 20 wherein said cycloaliphatic acrylate is further defined as cyclohexyl acrylate.

24. A coating composition as set forth in claim 20 wherein said cycloaliphatic methacrylate is further defined as cyclohexyl methacrylate.

25. A coating composition as set forth in claim 20 wherein said alkyl acrylic acids are selected from the group consisting of acrylic acid, methacrylic acid, ethacrylic acid, maleic acid, fumaric acid, itaconic acid, crotonic acid, and mixtures thereof.

26. A coating composition as set forth in claim 1 wherein said at least one vinylaromatic hydrocarbon monomer (A)(I)(b) is selected from the group consisting of α-methylstyrene, diphenylethylene, dinapthaleneethylene, and mixtures thereof.

27. A coating composition as set forth in claim 1 wherein said plurality of ethylenically unsaturated monomers (A)(II)(a) are selected from the group consisting of styrene, butyl acrylate, butyl methacrylate, 2-ethylhexyl methacrylate, 2-hydroxyethyl methacrylate, cyclohexyl methacrylate, glycidyl acrylate, glycidyl methacrylate, carbonate-modified glycidyl acrylate, carbonate-modified glycidyl methacrylate, and mixtures thereof, such that said plurality of ethylenically unsaturated monomers (A)(II)(a) are different than (A)(I)(a) and at least one of said plurality (A)(II)(a) includes said carbonate functional group.

28. A coating composition as set forth in claim 1 further comprising the reaction product of an anionic surfactant.

29. A coating composition as set forth in claim 1 wherein said first block (A)(I) has a molecular weight of from 1,000 to 20,000.

30. A coating composition as set forth in claim 1 having a non-volatile content of from 20 to 60 percent non-volatile by weight.

31. A coating composition as set forth in claim 1 having an average particle size of less than or equal to 200 nm.

32. A coating composition as set forth in claim 1 wherein said copolymer (A) ha a molecular weight of from 5,000 to 2,000,000.

33. A method of preparing a curable, water-based coating composition, said method comprising the steps of:
  (A) forming a first block that is the reaction product of at least one ethylenically unsaturated monomer and at least one vinylaromatic hydrocarbon monomer;
  (B) polymerizing a second block having at least one carbonate functional group with the first block to establish a water-based copolymer;
  (C) converting the at least one carbonate functional group in the second block of the water-based copolymer into at least one carbamate functional group; and
  (D) combining the water-based copolymer with at least one cross-linking agent that is reactive with the carbamate functional group and dispersible in water.

34. A method as set forth in claim 33 wherein the at least one cross-linking agent (B) is selected from the group consisting of water-dispersible aminoplasts, water-dispersible polymers having acrylamide groups, and water-dispersible polymers having methylol or alkoxymethyl groups, and mixtures thereof.

35. A method as set forth in claim 34 wherein the water-dispersible aminoplasts are selected from the group of melamine formaldehyde resins having a methylol group, an alkoxymethyl group, or both, which are reactive with the carbamate functional group.

36. A method as set forth in claim 33 wherein the step of (C) converting the at least one carbonate functional group in the second block of the water-based copolymer into the at least one carbamate functional group is further defined as reacting an ammonia-containing compound selected from the group consisting of ammonia, ammonium hydroxide, and mixtures thereof, with the carbonate functional group to convert the carbonate functional group into the carbamate functional group.

37. A method as set forth in claim 33 wherein the steps of (A)–(C) are conducted at a temperature between 50° C. and 100° C.

38. A method as set forth in claim 33 wherein the step of polymerizing the at least one ethylenically unsaturated monomer and the at least one vinylaromatic hydrocarbon monomer is conducted over time from 1 to 8 hours.

39. A method as set forth in claim 33 wherein the step of (A) forming the first block further includes the step of adding a neutralizing agent selected from the group consisting of dimethylethanolamine, amino methyl propanol, ammonia, and mixtures thereof, to the at least one ethylenically unsaturated monomer and the at least one vinylaromatic hydrocarbon monomer to form the first block of the water-based copolymer.

40. A method as set forth in claim 33 wherein the step of (A) forming the first block further includes the step of adding an initiator selected from the group consisting of inorganic persulfates, dialkyl peroxides, hydroperoxides, peresters, and mixtures thereof, to the at least one ethylenically unsaturated monomer and the at least one vinylaromatic hydrocarbon monomer to form the first block of the water-based copolymer.

41. A method as set forth in claim 33 wherein the at least one ethylenically unsaturated monomer is selected from the group of compounds consisting of aliphatic acrylates, aliphatic methacrylates, cycloaliphatic acrylates, cycloaliphatic methacrylates, alkyl acrylic acids, and mixtures thereof, each of the compounds having up to 20 carbon atoms in the alkyl radical.

42. A method as set forth in claim 33 wherein the at least vinyl aromatic hydrocarbon monomer is selected from the group consisting of α-methylstyrene, diphenylethylene, dinapthaleneethylene, and mixtures thereof.

43. A method as set forth in claim 33 wherein the step of (B) polymerizing the second block having at least one carbonate functional group with the first block is further defined as polymerizing a plurality of ethylenically unsaturated monomers with the first block, wherein at least one of the plurality includes the carbonate functional group that is converted into the carbamate functional group, to form the second block of the water-based copolymer.

44. A method as set forth in claim 43 wherein the step of polymerizing the plurality of ethylenically unsaturated monomers with the first block is conducted over time from 1 to 8 hours.

45. A method as set forth in claim 43 wherein the plurality of ethylenically unsaturated monomers are selected from the group consisting of styrene, butyl acrylate, butyl methacrylate, 2-ethylhexyl methacrylate, 2-hydroxyethyl methacrylate, cyclohexyl methacrylate, glycidyl acrylate, glycidyl methacrylate, carbonate-modified glycidyl acrylate, carbonate-modified glycidyl methacrylate, and mixtures thereof, such that at least one of the plurality includes the carbonate functional group.

46. A method as set forth in claim 34 wherein the step of (D) combining the water-based copolymer with the at least one cross-linking agent further includes the step of reacting the methylol and the alkoxymethyl groups of the melamine formaldehyde resins with the at least one carbamate functional group.

47. A method as set forth in claim 33 wherein the step of (C) converting the at least one carbonate functional group in the second block of the water-based copolymer into the at least one carbamate functional group is conducted over time from 1 to 4 hours.

48. A method as set forth in claim 33 wherein the step of (D) combining the water-based copolymer with at least one cross-linking agent further includes the step of adding an anionic surfactant to guarantee the dispersibility of the cross-linking agent in water.

49. A method of preparing a cured film of a water-based coating composition, said method comprising the steps of:
(A) forming a first block that is the reaction product of at least one ethylenically unsaturated monomer and at least one vinylaromatic hydrocarbon monomer;
(B) polymerizing a second block having at least one carbonate functional group with the first block to establish a water-based copolymer;
(C) converting the at least one carbonate functional group in the second block of the water-based copolymer into at least one carbamate functional group;
(D) combining the water-based copolymer with at least one cross-linking agent that is dispersible in water and reactive with the carbamate functional group to form the water-based coating composition;
(E) applying the water-based coating composition to a substrate; and
(F) curing the water-based coating composition to form the cured film.

50. A method as set forth in claim 49 wherein the step of (E) applying the water-based coating composition to the substrate is further defined as spraying the water-based coating composition on to the substrate.

51. A method as set forth in claim 49 wherein the step of (F) curing the water-based coating composition is further defined as reacting the cross-liking agent with the at least one carbamate functional group to form the cured film of the water-based coating composition.

52. A method as set forth in claim 51 wherein the cross-linking agent is a water-dispersible aminoplast selected from the group of melamine formaldehyde resins having a methylol group, an alkoxymethyl group, or both, which are reactive with the carbamate functional group.

53. A method as set forth in claim 52 wherein the step of reacting the cross-linking agent with the at least one carbamate functional group is further defined as reacting the methylol and alkoxymethyl groups of the melamine formaldehyde resins with the at least one carbamate functional group.

54. A method as set forth in claim 51 wherein the step of reacting the cross-linking agent with the at least one carbamate functional group is conducted at a temperature between 100° C. and 175° C.

55. A method as set forth in claim 49 wherein the at least one ethylenically unsaturated monomer is selected from the group of compounds consisting of aliphatic acrylates, aliphatic methacrylates, cycloaliphatic acrylates, cycloaliphatic methacrylates, alkyl acrylic acids, and mixtures thereof, each of the compounds having up to 20 carbon atoms in the alkyl radical.

56. A method as set forth in claim 49 wherein the at least vinyl aromatic hydrocarbon monomer is selected from the group consisting of α-methylstyrene, diphenylethylene, dinapthaleneethylene, and mixtures thereof.

57. A method as set forth in claim 49 wherein the step of (B) polymerizing the second block having at least one carbonate functional group with the first block is further defined as polymerizing a plurality of ethylenically unsaturated monomers with the first block, wherein at least one of the plurality includes the carbonate functional group that is converted into the carbamate functional group, to form the second block of the water-based copolymer.

58. A method as set forth in claim 57 wherein the plurality of ethylenically unsaturated monomers are selected from the group consisting of styrene, butyl acrylate, butyl methacrylate, 2-ethylhexyl methacrylate, 2-hydroxyethyl methacrylate, cyclohexyl methacrylate, glycidyl acrylate, glycidyl methacrylate, carbonate-modified glycidyl acrylate, carbonate-modified glycidyl methacrylate, and mixtures thereof, such that at least one of the plurality includes the carbonate functional group.

* * * * *